(12) United States Patent
Kilcoin et al.

(10) Patent No.: US 6,395,235 B1
(45) Date of Patent: May 28, 2002

(54) DEVICES AND METHODS FOR ACCESSING REACTION VESSELS

(75) Inventors: Christopher Kilcoin, Los Altos Hills, CA (US); Terry Long, Tucson, AZ (US); Jan Hughes, Belmont; James Wasson, Los Altos, both of CA (US)

(73) Assignee: Argonaut Technologies, Inc., San Carlos, CA (US)

( * ) Notice: Subject to any disclaimer, the term of this patent is extended or adjusted under 35 U.S.C. 154(b) by 0 days.

(21) Appl. No.: 09/378,664

(22) Filed: Aug. 20, 1999

Related U.S. Application Data
(60) Provisional application No. 60/116,908, filed on Jan. 22, 1999, and provisional application No. 60/097,511, filed on Aug. 21, 1998.

(51) Int. Cl.⁷ .............................................. B01L 11/00
(52) U.S. Cl. .................... 422/103; 137/597; 422/63; 422/104; 422/129
(58) Field of Search ........................ 422/99, 100, 101, 422/103, 104, 63, 129, 131, 916, 937, 938; 436/43, 47, 48, 174, 180; 137/597, 883, 884; 73/863.81

(56) References Cited

U.S. PATENT DOCUMENTS

| | | |
|---|---|---|
| 1,346,137 A | 7/1920 | Silverthorne |
| 2,594,621 A | 4/1952 | Derrick ...................... 128/278 |
| 3,019,815 A | 2/1962 | Lenardon et al. ......... 137/612.1 |
| 3,613,729 A | 10/1971 | Dora ...................... 137/624.18 |
| 3,951,167 A | 4/1976 | Howell et al. .............. 137/608 |
| 4,008,736 A | 2/1977 | Wittmann-Liebold et al. ........................... 137/606 |
| 4,168,724 A | 9/1979 | Graffunder et al. ......... 137/606 |
| 4,304,257 A | 12/1981 | Webster ...................... 137/559 |
| 4,558,845 A | 12/1985 | Hunkapiller ................ 251/331 |
| 4,597,412 A | 7/1986 | Stark ........................... 137/606 |
| 4,671,329 A | 6/1987 | Kovacevich, Jr. .............. 141/5 |
| 4,676,283 A | 6/1987 | Caldwell ........................ 141/4 |
| 4,726,932 A | 2/1988 | Feier et al. ................. 422/103 |
| 4,746,491 A | 5/1988 | Öhlin ......................... 422/103 |
| 4,753,265 A | 6/1988 | Barrett et al. ............... 137/554 |
| 4,867,354 A | 9/1989 | Schreiber .................... 222/521 |
| 5,019,348 A | 5/1991 | Ohms et al. .................. 422/63 |
| 5,100,626 A | 3/1992 | Levin |

(List continued on next page.)

FOREIGN PATENT DOCUMENTS

| | | |
|---|---|---|
| GB | 634222 | 3/1950 |
| WO | WO 97/14041 | 4/1997 |
| WO | WO 98/06627 | 2/1998 |
| WO | WO 98/56506 | 12/1998 |
| WO | WO 99/20395 | 4/1999 |

*Primary Examiner*—Joseph W. Drodge
(74) *Attorney, Agent, or Firm*—Townsend and Townsend and Crew LLP

(57) ABSTRACT

Devices and methods are provides for delivering fluids into reaction vessels. The present device is an interface head which allows a user to add reagents and wash solvents to a reaction vessel. Typically, the interface head can engage a plurality of these reaction vessels mounted in a cassette or frame and is adapted to removably engage passages leading into the reaction vessel. The interface head allows a user to manually inject materials into the plurality of passageways in the head which are fluidly coupled to the reaction vessel. In one embodiment, the interface head has a septa valve which opens and closes inlets of the plurality of passageways. The septa valve comprises an elongate member with a septum portion and a plurality of septum ports. The elongate member is slidable between a first position wherein at least one inlet of the passageways in the interface head is sealed by the septum portion and a second position wherein said at least one inlet is aligned with one of the ports to allow delivery of materials from the inlet into the reaction vessel. The septum portion is penetrable by needles and thus allows access for needle/syringe type delivery devices.

23 Claims, 18 Drawing Sheets

U.S. PATENT DOCUMENTS

| | | | |
|---|---|---|---|
| 5,172,728 A | 12/1992 | Tsukazaki | 137/637.2 |
| 5,182,082 A | 1/1993 | Monthony et al. | |
| 5,259,423 A | 11/1993 | Simmel et al. | 141/1 |
| 5,273,718 A | 12/1993 | Sköld et al. | |
| 5,301,723 A | 4/1994 | Goode | 141/82 |
| 5,424,038 A | 6/1995 | Benz et al. | 422/100 |
| 5,503,805 A | 4/1996 | Sugarman et al. | 422/131 |
| 5,535,923 A | 7/1996 | Fujioka | 222/148 |
| 5,565,171 A | 10/1996 | Dovichi et al. | 422/68.1 |
| 5,605,666 A | 2/1997 | Goodale et al. | 422/103 |
| 5,609,826 A | 3/1997 | Cargill et al. | 422/99 |
| 5,660,792 A | 8/1997 | Koike | 422/63 |
| 5,665,975 A | 9/1997 | Kedar | 250/573 |
| 5,762,881 A | 6/1998 | Harness et al. | 422/132 |
| 5,765,591 A | 6/1998 | Wasson et al. | 137/597 |

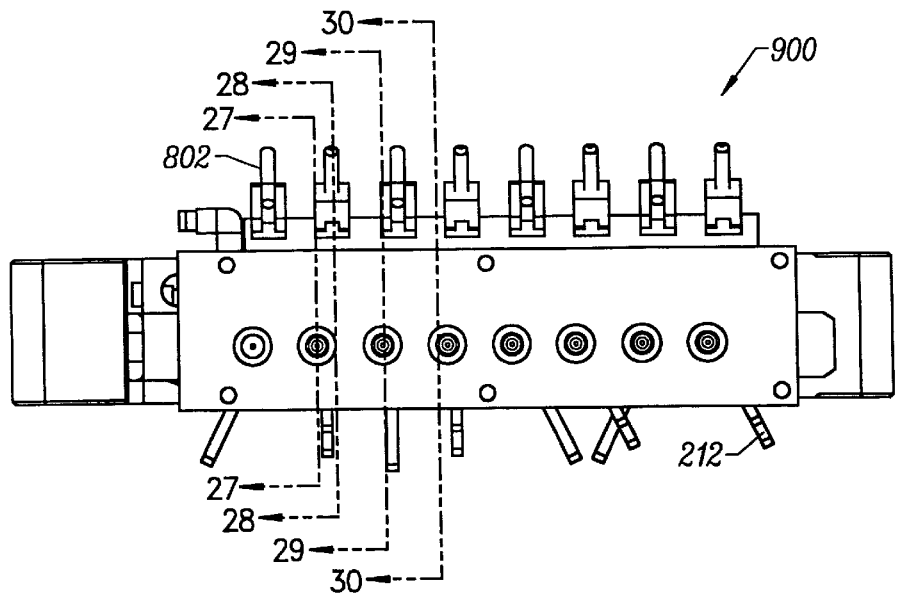
FIG. 26
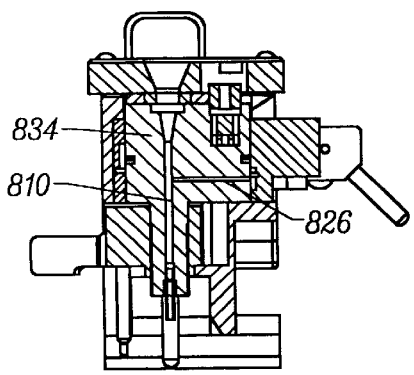 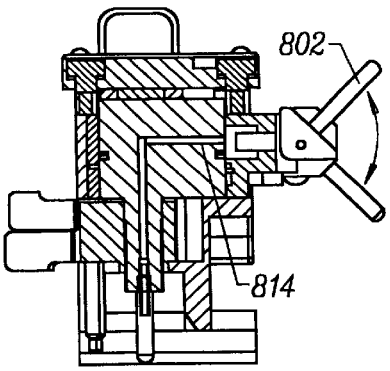
FIG. 27      FIG. 28
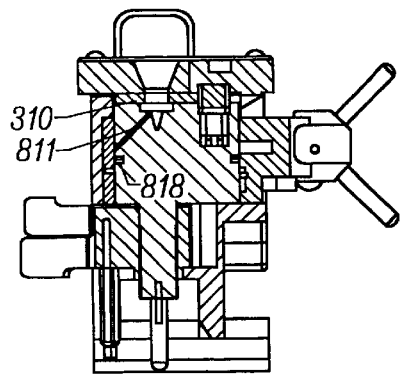 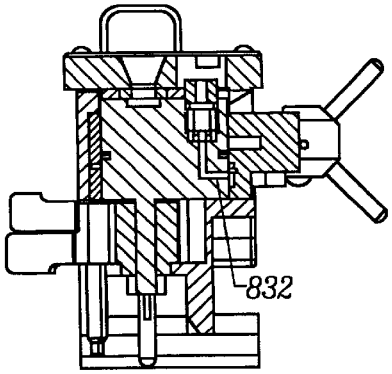
FIG. 29      FIG. 30

DEVICES AND METHODS FOR ACCESSING REACTION VESSELS

CROSS-REFERENCE TO RELATED APPLICATIONS

This application claims the benefit of the following Provisional Patent Applications: Systems and Methods for Accessing Reaction Vessels, application Ser. No. 60/097,511, filed Aug. 21, 1998; and Devices and Methods for Accessing Reaction Vessels, application Ser. No. 60/116,908, filed Jan. 22, 1999; the disclosures of which are incorporated by reference.

BACKGROUND OF THE INVENTION

The standard method for searching for new chemical compounds which can effectively modulate biological processes employs the screening of pre-existing compounds in assays which have been designed to test particular properties of the compound being screened. Similarly, in designing compounds having desired physiochemical properties for general chemical applications, numerous compounds must be individually prepared and tested.

To reduce the time and expense involved in preparing and screening a large number of compounds for biological activity or for desirable physiochemical properties, technology has been developed for providing libraries of compounds for the discovery of lead compounds. Current methods for generating large numbers of molecularly diverse compounds focus on the use of solid phase synthesis. The generation of combinatorial libraries of chemical compounds by employing solid phase synthesis is well known in the art. For example, Geysen, et al. (Proc. Natl. Acad. Sci. USA, 3998 (1984) describe the construction of multi-amino acid peptide libraries; Houghton, et al. (Nature, 354, 84 (1991) and PCT Patent Pub. No. WO 92/09300) describe the generation and use of synthetic peptide combinatorial libraries for basic research and drug discovery; Lam, et al. (Nature, 354, 82 (1991) and PCT Patent Pub. No. WO 92/0009 1) describe a method of synthesis of linear peptides on a solid support such as polystyrene or polyacrylamide resin.

The growing importance of combinatorial chemistry as an integral component of the drug discovery process has spurred extensive technological and synthetic advances in the field (Thompson, L. A.; Ellman, J. A. (1996) Chem. Rev. 96,555–600). Founded in peptide synthesis devised by Merrifield, solid phase chemistry has emerged as the preeminent method for construction of small molecule combinatorial libraries (see e.g. Merrifield, R. B. (1963) J. Am. Chem. Soc. 85, 2149–2154; (a) Terrett, N. K.; Gardner, M.; Gordon, D. W.; Kobylecki, R. J.; Steele, J. (1995) Tetrahedron 51(30), 8135–8173. (b) Gordon, E. M.; Barrett, R. W.; Dower, W. J.; Fodor, S. P. A.; Gallop, M. A. (1994) J. Med Chem. 37,1385–1401.).

Unfortunately, the generation of chemical compounds for combinatorial chemical libraries is a labor intensive process. Working with numerous reaction vessels concurrently is very difficult and time consuming. In the past, multiple solid phase reactions were conducted by heating a substrate attached to resin beads with appropriate reagents and solvents in a test tube immersed in a hot oil bath with a rotating magnetic stir bar. Draining was accomplished by pouring the contents of the test tube through a filter. Back and forth operation between reacting and draining operations was very tedious and potentially exposed the reaction mixture to air. Certain chemical processes also required that the chemical reagents be kept under an inert or anhydrous atmosphere to prevent reactive groups from reacting with molecular oxygen, water vapor, or other agents commonly found in air. Accordingly, there is a need for a device which would provide heating and/or cooling, mixing, a closed environment for moisture sensitive and air sensitive chemistries, easy draining, rapid liquid metering, and rinsing of a plurality of reaction vessels.

While certain chemical synthesizers are known in the art, these synthesizers fail to provide the desired features necessary to efficiently generate large numbers of chemical compounds.

SUMMARY OF THE INVENTION

The present invention is directed to an apparatus which is useful for the synthesis of chemical compounds, for example, for the preparation of multiple discrete compounds for combinatorial libraries of compounds. The present invention is useful for developing new drugs and chemical entities. The invention is useful for rapidly generating and systematically synthesizing large numbers of molecules that may vary in their chemical structure or composition. The invention is further useful for randomly generating a large number of candidate compounds, then later optimizing those compounds which exhibit the most desirable properties.

The present invention provides a interface head which allows a user to add reagents and wash solvents to a reaction vessel. Typically, the interface head can engage a plurality of these reaction vessels mounted in a cassette or frame and is adapted to removably engage passages leading into the reaction vessel. The interface head allows a user to manually inject materials into the plurality of passageways in the head which are fluidly coupled to the reaction vessel. The interface head has a septa valve which opens and closes inlets of the plurality of passageways. The septa valve comprises an elongate member with a septum portion and a plurality of septum ports. The elongate member is slidable between a first position wherein at least one inlet of the passageways in the interface head is sealed by the septum portion and a second position wherein said at least one inlet is aligned with one of the ports to allow delivery of materials from the inlet into the reaction vessel. The septum portion is penetrable by needles and thus allows access for needle/syringe type delivery devices.

Advantageously, the interface head may be manually operated to provide ease of use for operators. The interface head, of course, may also be adapted to be used with automated systems, such as mounted on a robotic manipulator. The interface, however, may also be used to add reagents to reaction vessels in situations where reagents in an automated procedure were left out or additional solvent washes are needed. The interface head may also be adapted to extract finished material from within reaction vessels. Guide pins may be provided to assist in the alignment of the interface head with a cassette or housing used to contain the reaction vessels. In some embodiments, the device is essentially a manifold having a septa valve providing access to a pipet or reagent injector, a coupling tube to interface with a passage leading to the reaction vessel, and a connector for actuating the valve of the reaction vessel.

In preferred embodiments, the interface head of the present invention allows for simultaneous introduction of wash fluids into a plurality reaction vessels. Typically, the reaction vessels each having a first upper port and a second upper port. The interface head is adapted to removably engage a plurality of passages each leading to the first upper port on each of the reaction vessels. A plurality of infusion passages in the interface head each have outlets adapted to be positioned to feed into the reaction vessels. Fluid introduced into a common infusion passage defined within the interface head may be simultaneously delivered into the infusion passages and into the reaction vessels. The interface head preferably has an interface tube adapted to form a radial seal with the passage leading to a first upper port of the reaction vessel, where the infusion passage is downstream of the common passage. Flow from the common passage into the infusion passages is preferably controlled by a membrane valve covering the common passage. The common passage is typically a groove on a surface of a manifold in the interface head. The interface head may also include a plurality of vent passages and a common vent passage defined by the interface head to remove materials from the plurality of reaction vessels.

In another aspect of the present invention, a method is provided for providing a substantially equal distribution of fluids to a plurality of reaction vessels during one fill cycle. The method includes flowing fluid along a common passage to the plurality of reaction vessels, where the common passage has a plurality of individual passageways opening into the reaction vessels. The reaction vessels are filled by using back pressure in the reaction vessels to direct flow to the reaction vessels with the least amount of fluid and back pressure. Back pressure in the reaction vessels are relieved by opening reaction vessel vent valves to allow the reaction vessels to continue filling with fluid. Without doing so, the back pressure may substantially slow delivery of fluids into the reaction vessels.

The structure and function of the preferred embodiments can best be understood by reference to the drawings. The reader will note that the same reference numerals appear in multiple figures. Where this is the case, the numerals refer to the same or corresponding structure in those figures.

BRIEF DESCRIPTION OF THE DRAWINGS

FIGS. 26–30 shows various views of an exemplary embodiment of an interface head according to the present invention.

DESCRIPTION OF THE SPECIFIC EMBODIMENTS

Figure 1A:
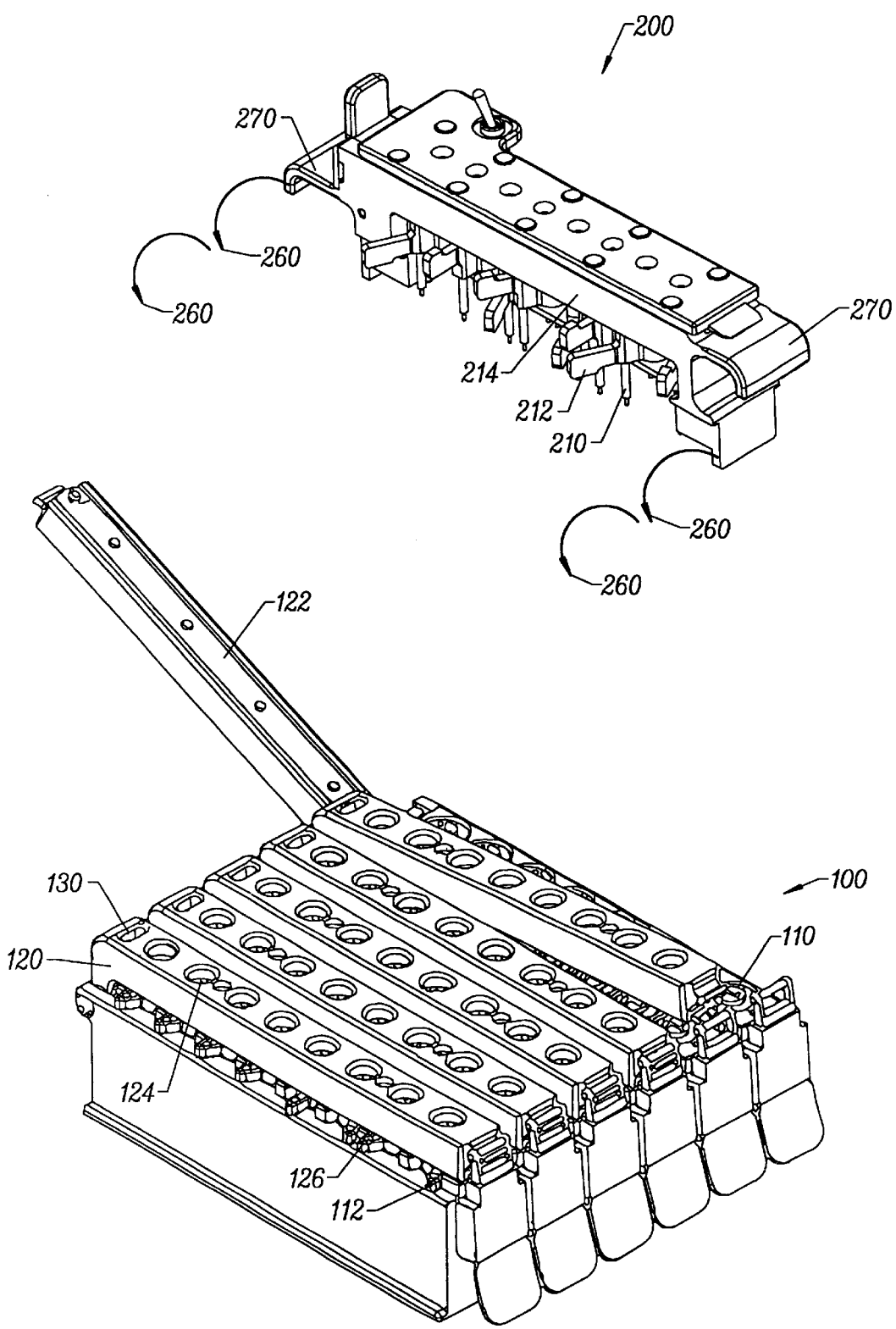
FIGS. 1A–1B show an interface head according to the present invention in use with a cassette holding a plurality of reaction vessels.

The present invention is directed to the synthesis of chemical compounds, such as for the generation of combinatorial chemical libraries. Specifically, the present invention provides an apparatus by which any variety of single compounds or combinatorial libraries may be created. The reaction apparatus of the present invention provides numerous advantages over known instrumentation. With large numbers of samples to process, the present apparatus facilitates the synthesis by allowing for common introduction of reagents and the simultaneous washing of a plurality of reaction vessels. This processing is preferably performed under an inert atmosphere in the reaction vessels. The present invention may also provide an agitator for uniformly and gently mixing the reaction media. Constant and evenly distributed heating and cooling may be provided during synthesis.

To facilitate the ease of operation, certain functions of the present invention, such as agitation of the reaction mixture, heating and cooling of the reaction vessel, inlet of inert atmosphere, introduction of reagents and solvents, rinsing and draining of reaction mixtures, and the like are preferably conducted by robotic automation or computer control. Accordingly, certain embodiments of the present invention are directed to the use of the apparatus which is partially or entirely conducted by robotic automation or under computer control.

As will be readily apparent to one skilled in the art the present invention is useful for the solid phase synthesis of organic compounds, including peptides. This device may be used for both solid phase chemistry and liquid-liquid chemistry, but solid phase chemistry is preferred. Alternatively, the present invention may be employed for the synthesis of organic compounds in the solution phase.

For the synthesis of compounds, appropriate starting materials may be attached to a support. Preferred support materials include solid polymeric materials, such as polyacrylamide, polydextran, polyethylene glycol, polystyrene, cellulose, sephadex, resins, combinations thereof, and the like. Alternate support materials include glass, acrylic, latex, and ceramics. Synthetic reactions may be conducted on the support-bound starting materials to obtain the desired compounds which may then be cleaved from the support.

As will be readily apparent to one skilled in the art, the present invention may be employed in essentially any synthetic reaction. For details, please see, commonly assigned U.S. patent application Ser. No. 09/176,615, filed Oct. 21, 1998, now abandoned, the full disclosure of which is incorporated herein by reference for all purposes.

A "combinatorial library" is a collection of compounds in which the compounds comprising the collection are composed of one or more subunits or monomeric units (i.e. synthons). The subunits may be selected from natural or unnatural moieties including amino acids, nucleotides, sugars, lipids, carbohydrates, dienes, dienopholes, and the like. The compounds of the combinatorial library differ in one or more ways with respect to the type(s), number, order or modification of the subunits comprising the compounds.

Combinatorial libraries generated by the methods of the present invention may be screened for pharmacologically or diagnostically useful compounds, as well as for desired physical or chemical properties. It will be clear to one skilled in the art that such screening may be conducted on a library of compounds which have been separated from the polyvalent support, or may be conducted directly on the library of compounds which are still linked to the polyvalent support.

Figure 1B:
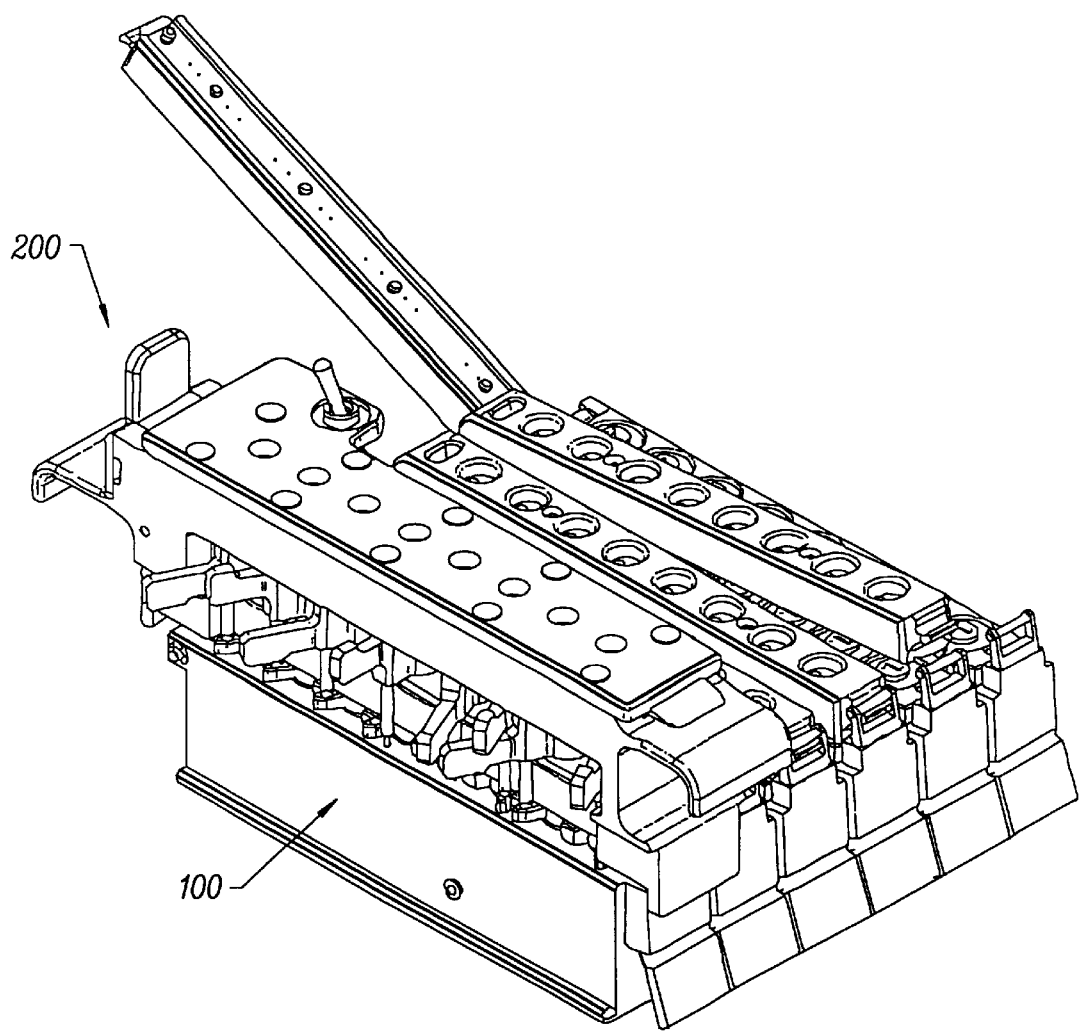
Figure 2:
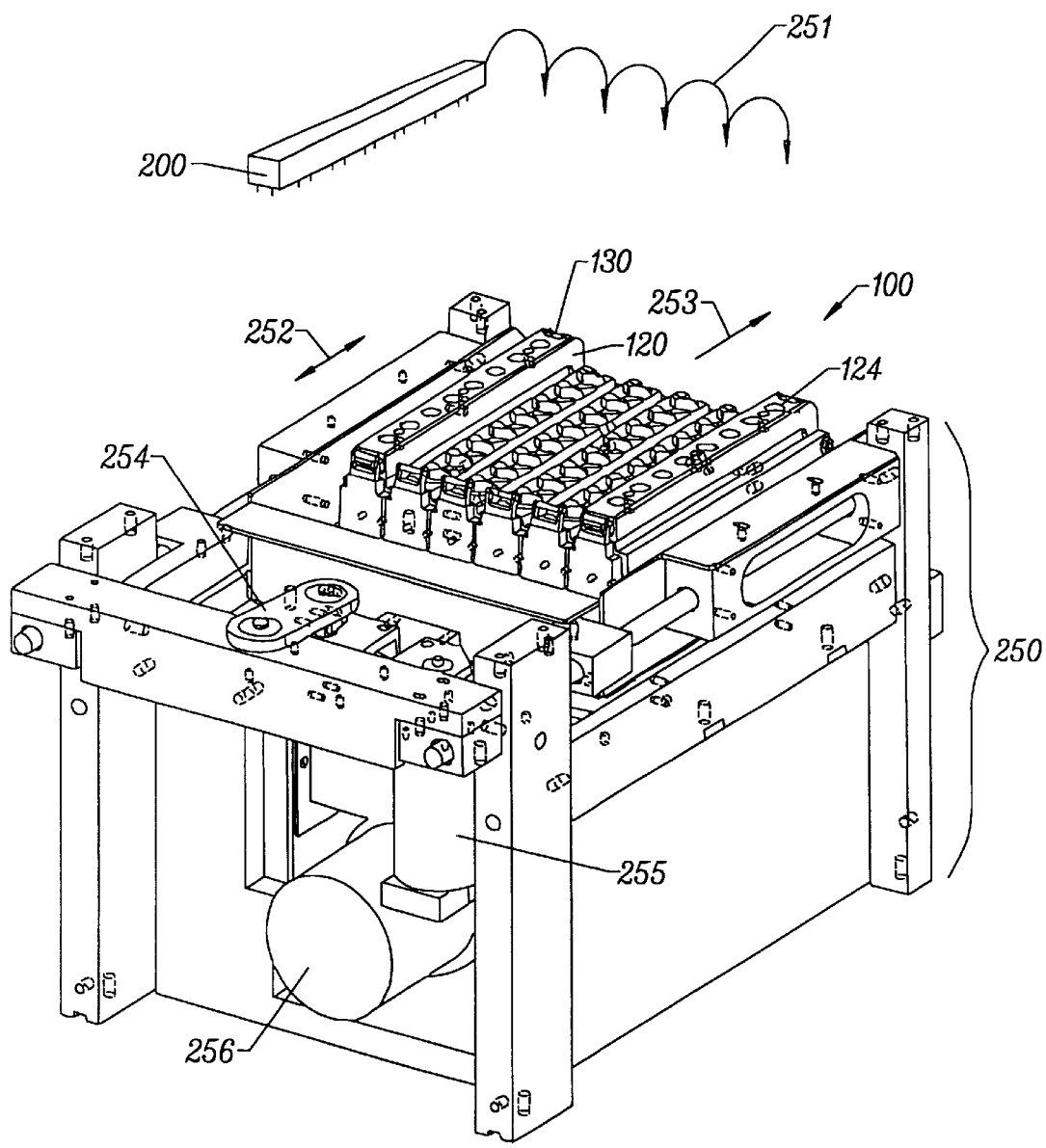
FIG. 2 is a perspective view of a cassette mounted on a heating and agitation unit.

Referring now to FIGS. 1A–1B and 2, a preferred embodiment of the present invention will now be described in detail. FIG. 1A shows one embodiment of a cassette 100 which may be used with wet chemistries or solid-state chemistries. The embodiment of cassette 100 shown in FIG. 1A contains 48 reaction vessels RV (FIGS. 3A–3B) for performing a variety of chemical syntheses. The cassette 100 contains reaction vessels which are particular suited for performing chemical reactions in an inert environment. Further details about the cassette 100 and the reaction vessels can be found in co-pending, commonly assigned U.S. patent application Ser. No. 09/095,731, filed on Jun. 10, 1998, the full disclosure which is incorporated herein by reference for all purposes.

In preferred embodiments, each reaction vessel has a cap 110 that includes a handle 112 that extends beyond the boundary of cassette lid or manifold 120. To provide fluid access into the reaction vessel, the cap 110 of the reaction vessel is rotated so that openings in the cap align with openings of 122 on the cassette lid 120 to define a fluid pathway into the reaction vessel. Thus, the rotation of the cap 110 seals and unseals of the opening into the reaction vessel.

In one embodiment, the present invention provides an interface head 200 that mates with the cassette lid 120. The interface head 200 is designed for infusion or injection of materials into the reaction vessels RV. FIG. 1A shows an embodiment of interface head 200 that mates with a single row of cassette lid openings 124 (sometimes referred to as liquid ports) on the cassette lid 120. Preferably, each cassette lid opening 124 can provide access to at least one reaction vessel RV. Although FIG. 1A and 1B shows an interface 200 that connects with an entire row of openings 124, it should be understood that the interface may be designed to mate with any number of cassette lid openings 124 and other configurations. For example, the interface head may be a square device that connects to four cassette lid openings in cassette lid 124, two of which are located on row of one cassette lid while the other two are located on an adjacent cassette lid. Preferably, each interface head 200 has at least one pin 210 that mates with the recess or opening 126 on handle 112 the reaction vessel cap 110. FIG. 1B shows the interface head 200 coupled to the cassette 100. The pin 210 typically has a handle 112 to allow for manual operation. As described in further detail below, the pin 210 may be rotatably moved as indicated by arrow 214 to adjust the position of handle 112, thus opening and closing the cap 110 over the reaction vessel.

As shown in FIG. 2, the cassette 100 is typically mounted on a heating and agitation unit 250. The interface head 200 is typically connected to the cassette lids 120 in a sequential manner as indicated by arrows 251. The cassette 100 is slightably engaged onto rails of the heating and agitation unit 250 as indicated by arrows 252. The cassette 100 may be removed from the agitation unit 250 by pulling it in the direction indicated by arrow 253. The cassette 100 may be aligned as shown in FIG. 2. It should be understood, however, that the cassette 100 may be designed in other embodiments to have configurations other than those shown in FIG. 2, such as having cassette lids 120 perpendicular to the orientation in FIG. 2. The heating and agitation unit 250 typically has a reciprocating cam mechanism 254 powered by motor 255 that moves the cassette 100 in the directions indicated by arrows 252. The unit 250 has a fan 256 that circulates and preferably recirculates a dry gas about the underside of the cassette 100. The gases may be either heated or cooled to create the desired temperature effect. Further details provided in commonly assigned, U.S. patent application Ser. No. 09/176,615 filed on Oct. 21, 1998, now abandoned, the full disclosure of which is incorporated herein by reference for all purposes.

The interface head 200 of FIG. 1A may be connected to the cassette 100 while the cassette is a stand-alone unit such as on a workbench, as shown in FIG. 1A, or alternatively when the cassette 100 is mounted on the heating and agitation unit 250 (FIG. 2). Preferably, the interface head 200 is pressed down onto the cassette lid 120 to engage the pins 210 with the openings 126 (FIG. 1A). As seen in FIG. 1A, the cassette 100 has a plurality of openings 130 which facilitate the alignment of the interface head 200 prior to the engagement of pins 210 with openings 126. Preferably, the user visually aligns pins 210 with openings 126 prior to lowering the interface 200 onto the cassette lid 120. For example, all of the handles 112 may be moved to a far right position while handles are moved into a corresponding position. The interface head 200 may be used in a serial manner as indicated by arrows 251 of FIG. 2 to provide access to a plurality of cassette lid openings 124. In one embodiment, such movement is provided by having a user manually lift and place the interface head 200 onto the cassette lid 120 through the use of handles 270. Of course, the interface head may also be designed for robotic manipulation to automate the chemical synthesis process. The interface head 200 may be made of a variety of materials such as aluminum, polyphenyl sulfide, or other thermal and stress resistant material.

Referring now to FIGS. 3A, 3B, 4, and 5, an interface head according to the present invention will be described in further detail. The interface head may assume a variety of configurations to fit the desired function. For example, there are interface heads which allow for the injection of fluid or other reagents into the reaction vessels. There are also interface heads which allow for the extraction of reagents or products from the reaction vessels. Additionally, there are interface heads which combine the functionality of both injection and extraction.

Figure 3A:
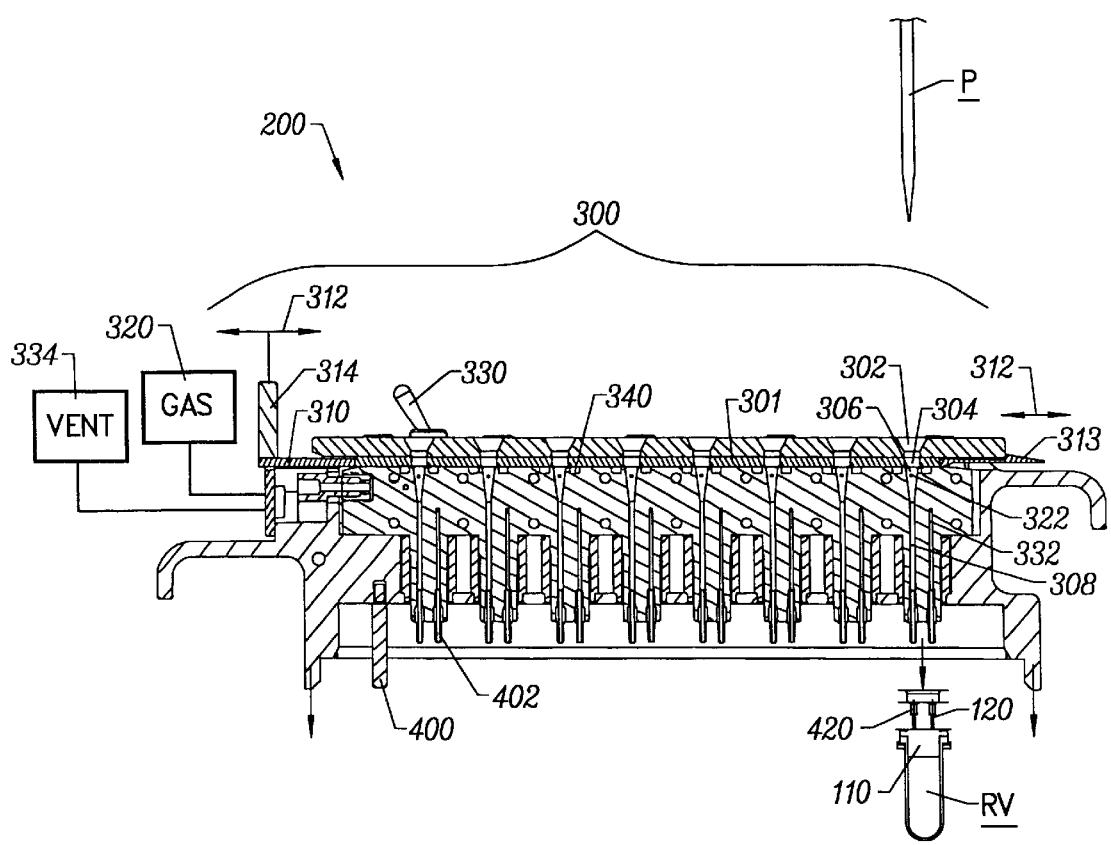
FIG. 3A is a cross-section of the interface head of FIGS. 1A–1B.
Figure 3B:
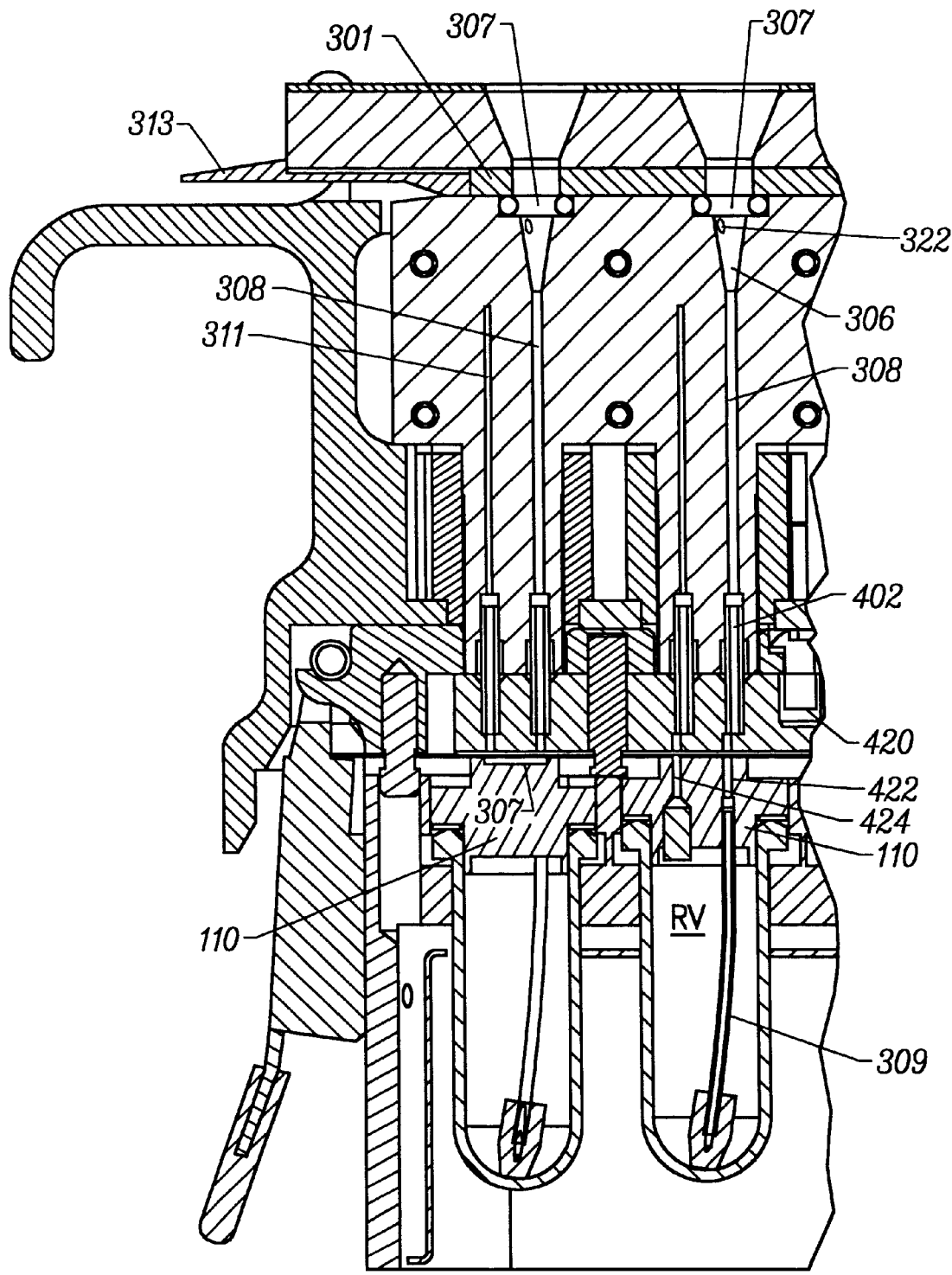
FIG. 3B is a partial cross-section of the interface head and cassette when they are mated together.

FIG. 3A shows the cross-section of an injection interface head 200 as it is about to engage a reaction vessel RV mounted below in cassette lid 120. As shown in FIG. 3A, the interface head 200 has a septa valve 300 that allows devices such as pipets and syringes to manually deliver reagents to the reaction vessels RV. When a syringe needle or other piercing device is used, the needle may pierce through the septum portion 301 of the septa valve. When a nonpenetrating member is used, the member such as a pipet P is be inserted through interface head opening 302 through septum opening 304 and into a preferably tapered passageway 306 with an inlet 307 (FIG. 3B). The distal tip of pipet P preferably forms a circumferential seal with tapered passageway 306. This seal minimizes the entry of contaminants into the reaction vessel when the vessel is operating in an inert environment. Alternatively, positive gas pressure supplied by source 320 may prevent the entry of airborne contaminants into the interface head 200.

In the present embodiment (FIG. 3A), septa valve 300 has a slide 310 which is an elongate member that can move in the manner indicated by arrow 312. Such movement, typically in the lateral direction, slides the septum ports or openings 304 to open or close passageway 306 and passageway 308. Specifically, the slide 310 is movable between a first position where the septum portion 301 of the slide 310 seals the inlet of passageway 306 and a second position where septum ports 304 are in alignment with the inlet of the passageway 306 and gas and solvent port 302. A distal end 313 having a wedge-shaped profile and handle 314 limit the range of motion of the septa valve slide 310. The slide 310 is preferably of sufficient length to control opening and closing of all openings 302 on the interface head 200. It should be understood of course, that in alternative embodiments, the septum valve does not necessarily cover all inlets 307 leading into the passageway 306.

Figure 4:
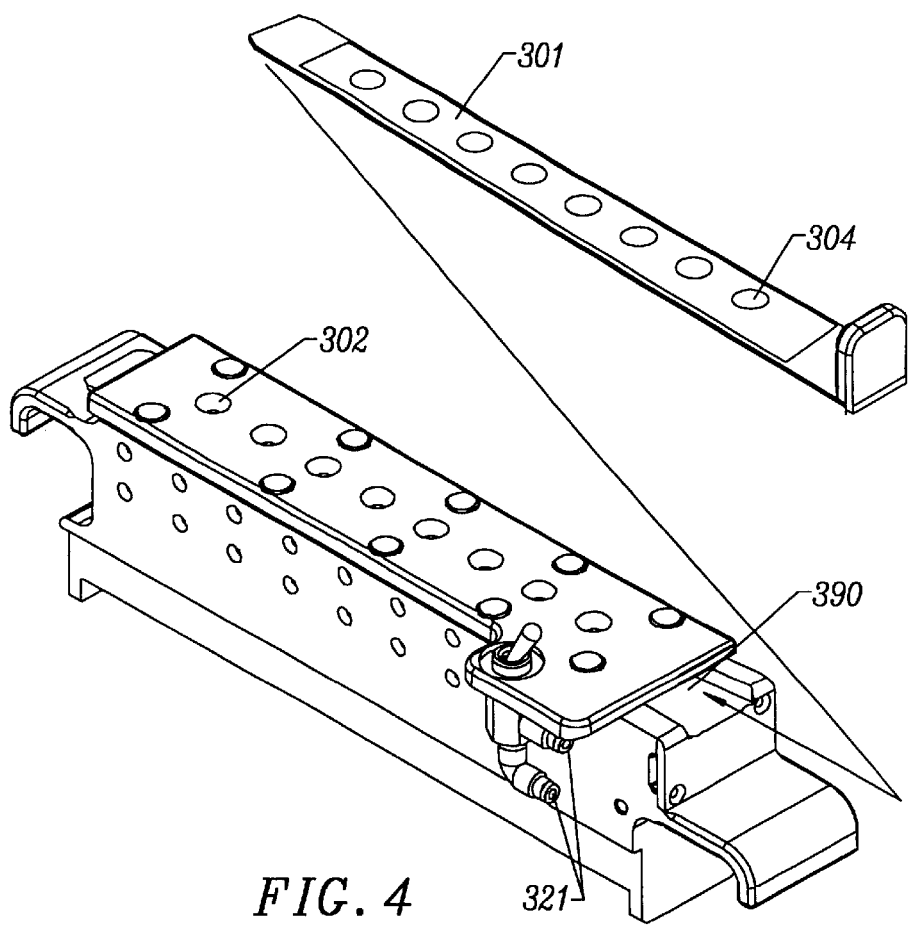
FIGS. 4–5 provide perspective views of the interface head of FIGS. 1A"1B.

After reagent has been delivered into inlet passageway 308, the slide 310 is preferably positioned to seal the opening 302. Typically, the injection head 200 is coupled to a pressurized gas source and to a gas vent. During operation of the injection head 200, fluid reagents are preferably supplied into inlet passageway 308 through the use of pipet P passing through septum opening 304 or by using a syringe to pierce the septum when septum opening 304 is in a closed position. Pressurized gas from source 320 may then be introduced through port 322 to blow reagents or wash solution from passageway 308 into the reaction vessel. Gas from source 320 may also be introduced into the tapered passageway 306 during injection to establish a positive pressure that prevents air from flowing into the reaction vessel during injection. FIG. 4 shows connections 321 for gas sources and vents. Preferably, the gases used are inert to the chemistries in the reaction vessel and will not interfere with chemical synthesis. The introduction of such inert gas is controlled by switch 330. When gas is flowing into the injection interface head 200, port 332 may allow for the exhaust of excess gas from the reaction vessel to a gas vent 334 that is fluidly coupled to the interface head. The septum is preferably made of a layer of sealing material such as silicone. This sealing material is typically bonded to a layer of chemically inert and protective material such as PTFE or Teflon® on each side so that the septum is inert to the chemistries used in synthesis but allows for penetration of a syringed needle through the septum portion 301. In one embodiment, the septum is 1/8" thick silicone bonded on both sides with 0.003" thick PTFE. Other known septum materials and thicknesses may also be used. A Kal-Rez O-ring 340 or similar elastomeric sealing member may be provided about each tapered passage 306 to facilitate a seal with slide 310.

Although the embodiment of FIG. 3A uses a slide 310 to open and close access to tapered passage 306, it should be understood that a variety of valving in septum devices may be used to control access. For example, the head 200 may have a rotatably activated valve that opens or closes access to into tapered passage 306. Such valving may be activated individually or coupled together simultaneous activation. The present invention may also use higher pressure pipettes or injection devices that can cleanly deliver the agents into the liquid into the reaction vessel without introducing contaminant gas or using solvent chase fluids (dilutes reagents) to deliver the entire amount of reagent into the reaction vessel. It is particularly desirable to deliver the entire amount of reagent into the reaction vessel due to the cost of some types of reagents.

Referring to FIG. 3A, the interface head 200 has a plurality of tubular members or interface tubes 402 designed to engage cavities or passages in the cassette lid 120. As the tubular members 402 engage passages 420 in the cassette lid 120, a circumferential seal is formed between the tubular members and the passages. As seen in FIG. 3B, the passages 420 lead to the first upper port 422 and second upper port 424 of the reaction vessel RV when cap 110 is in the open position. It should be understood of course, that in some alternative embodiments, the passages 420 may be incorporated into a portion of the cap 110 used with the reaction vessel RV. To facilitate alignment of the interface head 200 with the cassette 100, a guide pin 400 engages the opening 130 prior to fall engagement of the interface head against the lid 120 of the cassette. The guide pin 400 will prevent full engagement of the interface head against the cassette 100 when the head 200 is not properly aligned.

Referring now to FIG. 3B, a cross-section of an interface head 200 mounted on to a cassette 100 is shown. The interface head 200 has an inlet passageway 308 which allows fluid or other materials to be delivered towards the reaction vessel RV. As shown in FIG. 3B, the cap 110 has a first position (as shown in the reaction vessel on the right) where the inlet passage 308 is fluidly coupled to a tube 309 leading to the bottom of the reaction vessel RV. The fluid may be introduced from port 302 or from port 322. The fluid pathway into the reaction vessel RV comprises the tapered passage 306, the infusion passage 308, and those passages leading to reaction vessel tube 309.

As shown in the reaction vessel on the left, the cap 110 may be moved to a second position where access to the interior of the reaction vessel RV is sealed. In place of a fluid path leading to the interior of the reaction vessel, the cap 110 has a groove 307 defines a U-shaped fluid path with the inlet passage 308 and vent passage 311. Fluid flow through these passages with the cap 110 in the second position is shown by arrow 308. Hence, when the cap is in the first position, materials may be delivered or extracted from the interior of the reaction vessel. When the cap 110 is in the second position, the U-shaped fluid path allows the passages 302 and 306 to be washed with solvents to create a cleaned fluid path without residual materials that may effect the next reagent delivery.

FIG. 4 shows the slide 310 of the septa valve 300 removed from the interface head 200. The septa ports 304 on the slide 310 are typically arranged in a linear array, corresponding to the positions of the openings 302 in the interface head 200. The septum portion 301 of slide 310 preferably surrounds those areas around the ports 304. The slide 310 is received in slot 390 in the interface head 200 and may be reciprocated as indicated by arrow 312 in FIG. 3A.

Figure 5:
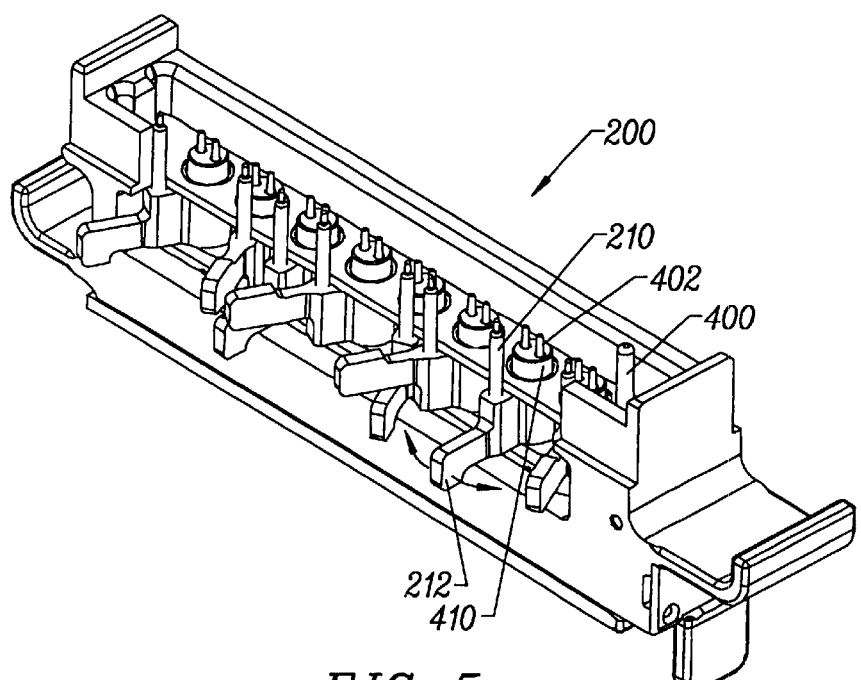

FIG. 5 shows the underside of injection manifold 200 and in further detail. As shown in the figure, alignment pin 400 preferably extends beyond the lower end of the connectors 402. As shown in FIG. 1A, the alignment pin 400 will fit into recess 130 when the interface head 200 is properly positioned to engage the cassette lid 120. This alignment will cause pin 400 to contact the upper surface of cassette lid 120 and prevent meeting of the interface head 200 with the cassette lid 120.

As seen in FIG. 5, the handle 212 and pin 210 rotate about the cylindrical structure 410 supporting the connectors 402. This provides the proper range motion for pin 210 when it is engaged with handle 112 of the valve cap 110. As shown in FIG. 3A, when the interface head 200 is lowered down to the cassette lid 120 and reaction vessel RV, the connectors will slidably engage receiving passages 420 in the cassette 100. Interference of approximately 0.003" to 0.006" provide a seal between the connector 402 and the passage 420. Preferably this seal is a radial seal between the side walls of the connector 402. The tube may have a diameter between about 0.080–0.100", preferably about 0.090" diameter. The connector 402 is preferably made of a resilient, chemically inert material such as Teflon® or specifically FEP (Fluorinated Ethylene Propylene). Other fluoropolymers such as PTFE (Polytetrafluoroethylene), ETFE (Tefzel), and PFA may also be used. This provides for a reliable seal while maintaining this fluid pathway inert to the chemistries used in chemical synthesis. Further details can be found in copending, commonly assigned U.S. patent application Ser. No. 09/095,731 previously incorporated herein by reference.

Figure 6:
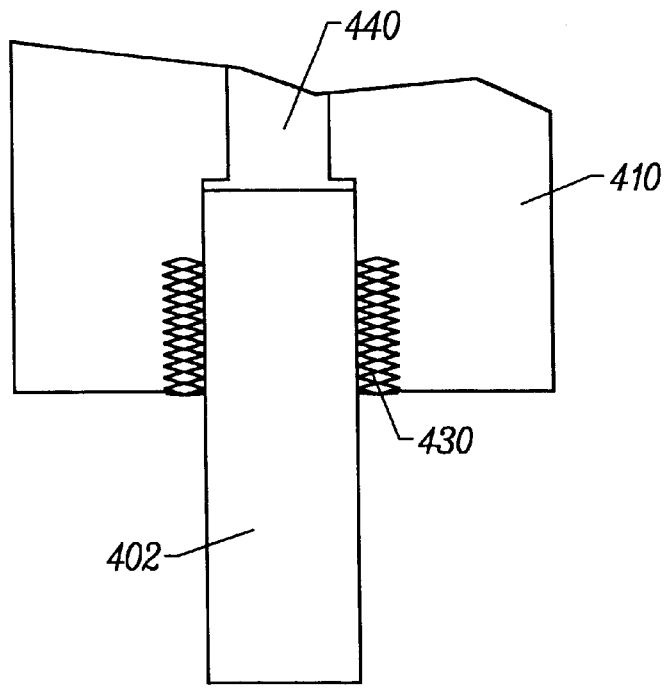
FIGS. 6–10 provide views of tubular members according to the present invention used with the interface head.

Referring to FIG. 6, preferred embodiments of the connector 402 comprise a smooth extruded tube of FEP. FEP is a material which cannot be easily reshaped or drilled without causing brittleness or an unsmooth surface, except in an extrusion process. Accordingly, the present invention, uses an extruded tube which is inserted into support 410. The connector 402 is typically press-fit into the support 410 and is preferably a non-piercing member. An exemplary embodiment, threading 420 such as that provided by an internally and externally threaded annular body is used to hold the connector to the support body 410 during coupling an decoupling with the cassette 100. Excessive temperature variation such as between 150° C. minus 40° C., of the cassette 110, may cause the passage 420 to tightly grip the connector 402 when the interface head is being decoupled. This may cause the connector 402 to be pulled form the support 410. Threads 430 provide additional support to the connector 402. It should be noted that the inert pathway is maintained since a proximal end of connector 402 extends beyond the threaded portion 430 to connect with port 440 in the support 410.

Figure 7:
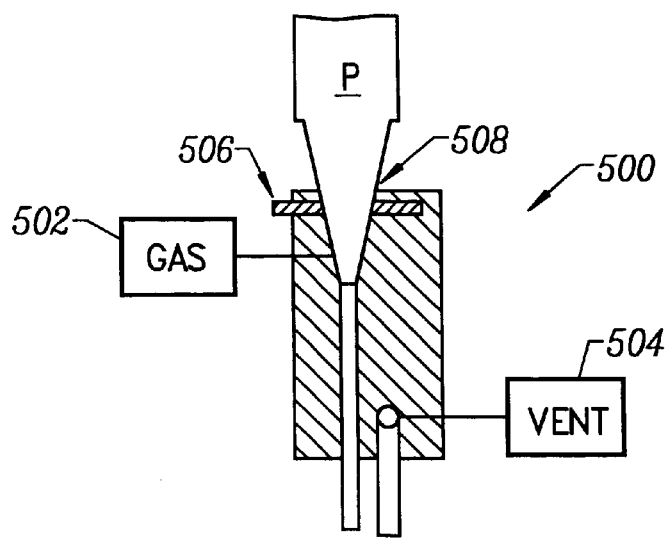

Referring now to FIG. 7, an alternative embodiment of the present invention will now be described. FIG. 7 shows an interface head 500 for use with a single cassette lid opening 124. The interface head 500 may be adapted to fit about the distal end of a pipe head P or an injection syringe (not shown). The head 500 may be connected to a gas source 502 and a vent 504 and in a manner similar to the interface head 200 best described in FIG. 3A. The interface head 500 may also have a valve 506 for sealing the upper opening 508 of the interface head 500. Such a device may be adapted for use with a variety of injection devices used to introduce free agents. The head 500 may also be adapted for extraction purposes.

Figure 8:
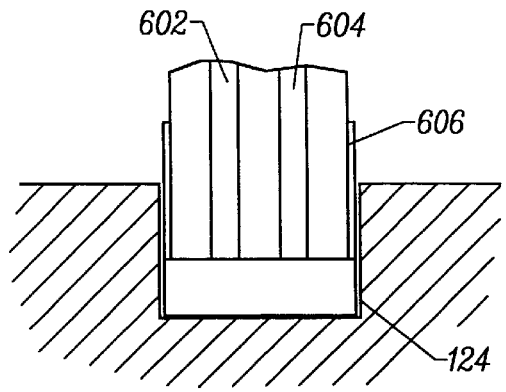
Figure 9:
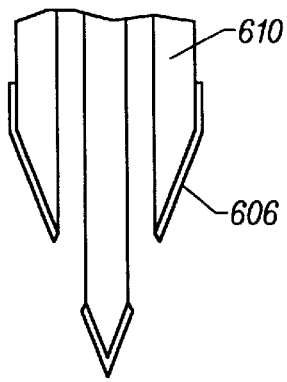
Figure 10:
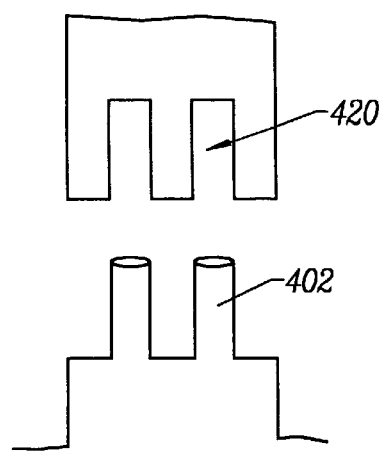

FIGS. 8–10 show alternative designs for fluid delivery connectors used on the interface head to engage the cassette 100. FIG. 8 shows a block of inert material such as Teflon® having 2 lumens 602 and 604. An external annular ring 606 of resilient Teflon® material such as FEP may be used to provide a radial seal with opening 124 while maintaining the chemical inertness of the device. FIG. 9 shows similar embodiment having a pointed distal tip which would engage a matching recess (not shown) to receive the connector 610. As can be seen in FIG. 9, external layer of resilient inert material 606 is also provided. The further alternative embodiment shown in FIG. 10, the designs are reversed where the interface head has passages 420 or female connectors while the cassette has connectors 402 or male connectors. It should be understood that a variety of slidable connectors may be used, preferably providing a reliable seal and inert chemistry. For example, the device may use O-rings located on the distal tip of connectors 402 to provide a positive compressive seal with passage 420. Such press or force may be provided by clamps or other locking mechanisms provided the exterior surface of the interface head.

Figure 11:
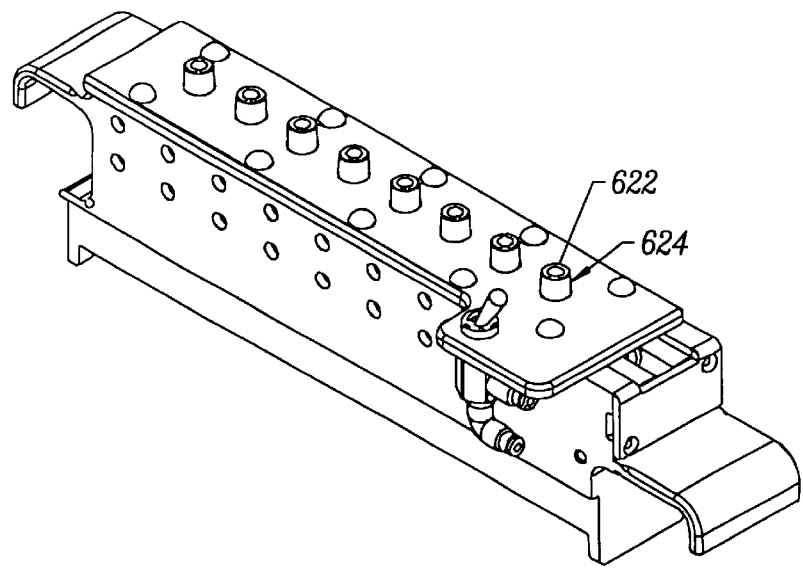
FIGS. 11–12 show an alternative embodiment of the interface head dedicated for extracting materials from reaction vessels.
Figure 12:
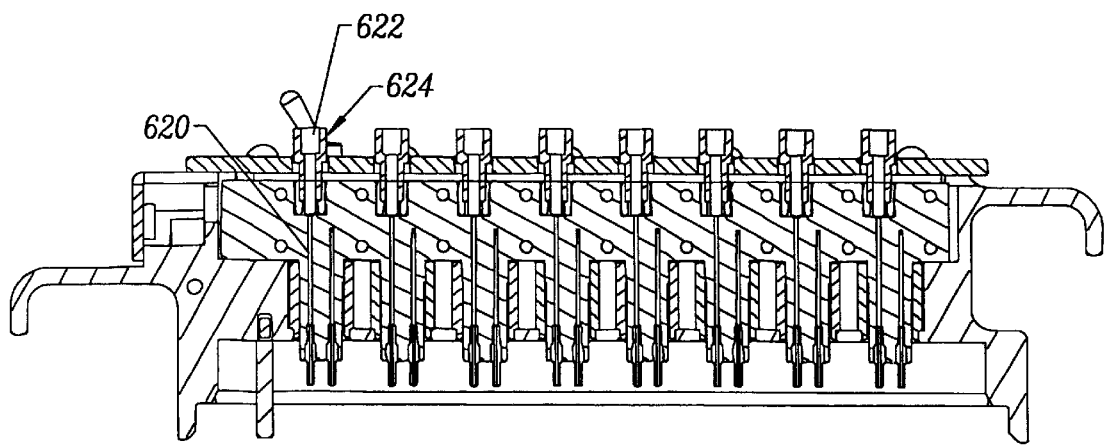

Referring to FIGS. 11 and 12, when a head is adapted for extraction of liquid from the reaction vessel, pressure is provided into the reaction vessel so as to force fluid out of vent passage 620 and up through opening 622. Preferably, connectors 624 which may be permanently fixed or removably coupled to opening 302 will provide an inert pathway from the reaction vessel to the extraction container. As described earlier, an interface head may be designed specifically for injection, for extraction, or for both injection/ extraction. When combined, the passage 306 may be designed to accommodate both the distal tip of a pipet and a connector 624. For example, the passage 306 may retain its tapered configuration but have a latch that can secure the connector 624 to the passageway.

Figure 13:
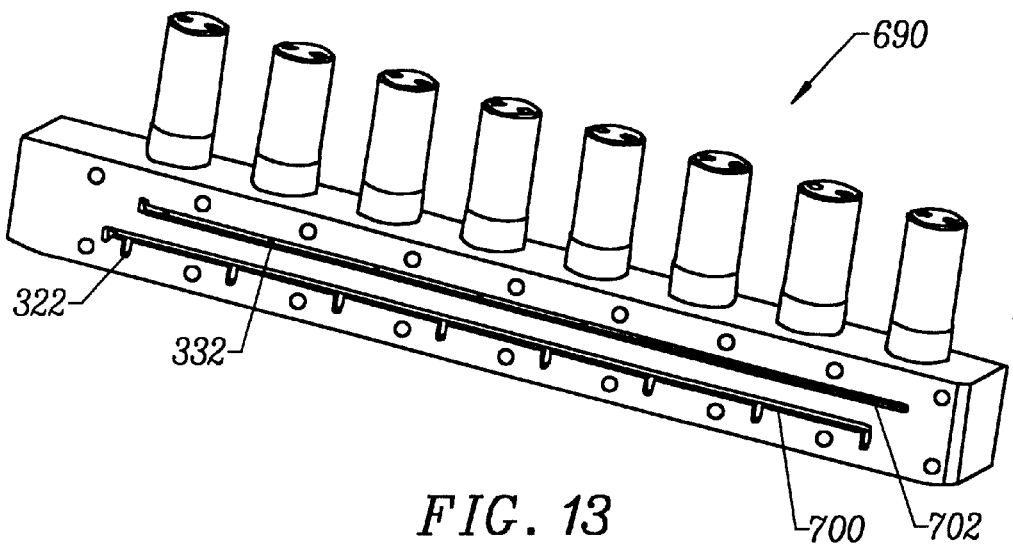
FIGS. 13–18 shows various views of a manifold used in the interface head of FIGS. 1A and 1B.
Figure 14:
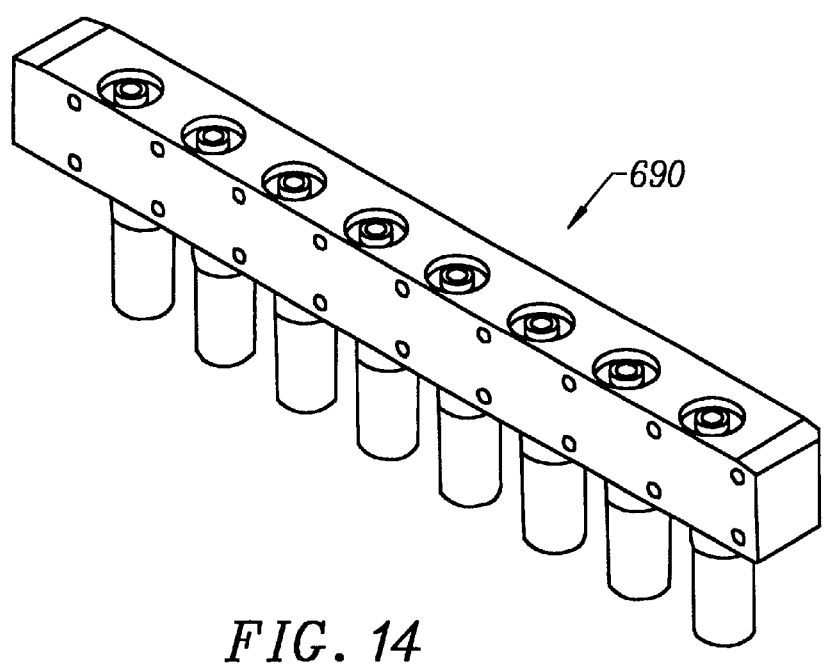
Figure 17:
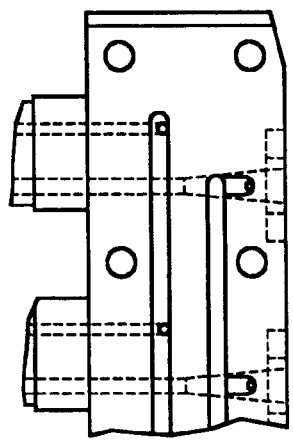
Figure 16:
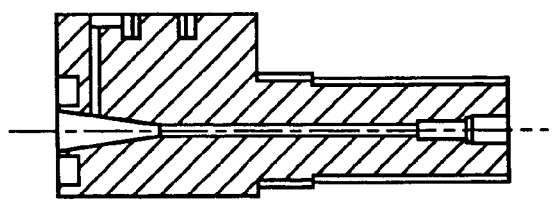
Figure 15:
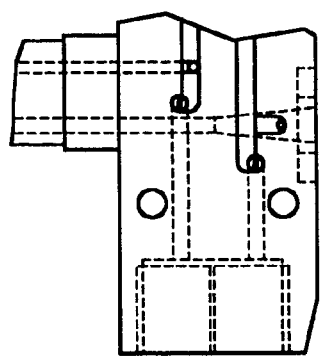
Figure 18:
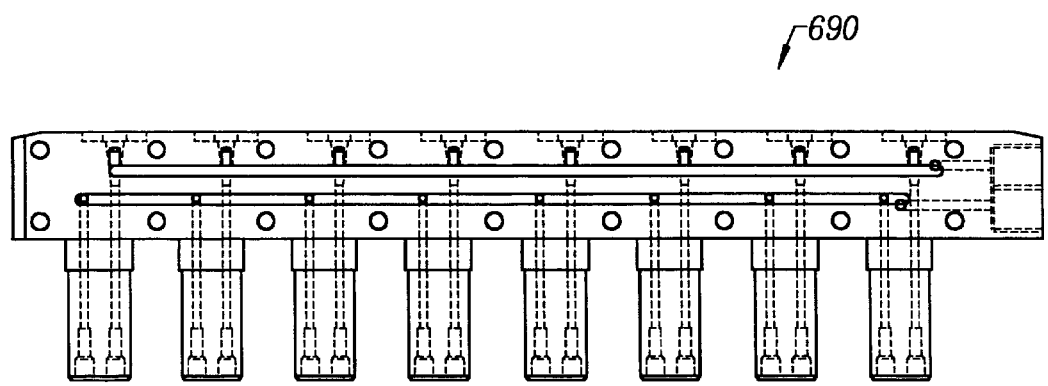

Referring to FIG. 13, the interface manifold 690 will now be described. FIG. 13 shows the common injection passage 700 in manifold 690 which connect the gas injection ports 322 for each passage leading to a reaction vessel. A common vent passage 702 which connects the gas vent ports 332 for each passage leading from a reaction vessel. By controlling which reaction vessel cap 110 is opened (by using interface valve handle 212), the gas from passage 700 may be used to inject reagent into the reaction vessel. Alternatively, gas in passage 702 may cause liquid to be pushed out from the reaction vessel in an extraction process. FIGS. 14–18 show additional cross-sectional detail of the interface manifold 690.

Figure 19:
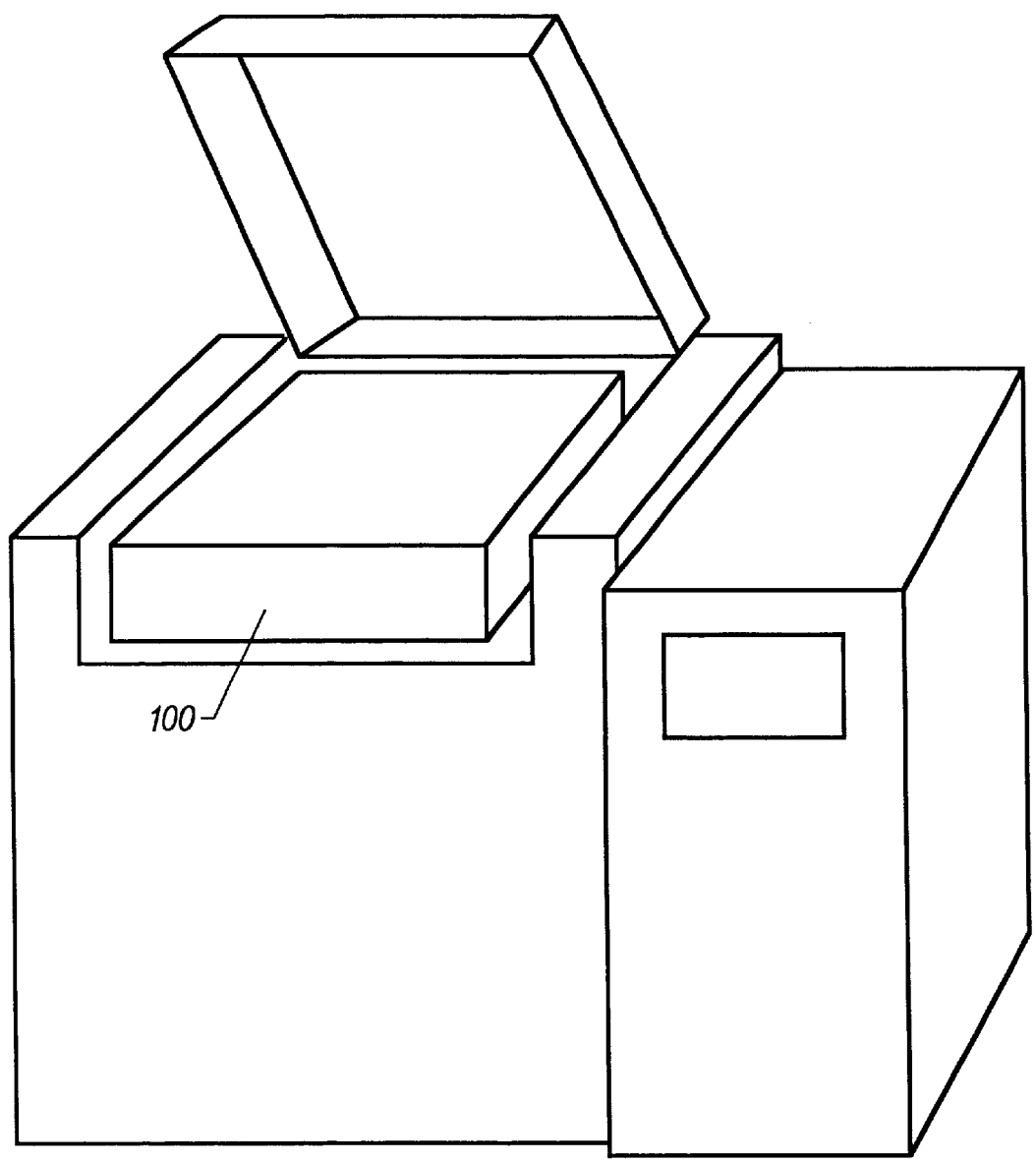
FIG. 19 is a perspective view of a housing for use with the heating and agitation unit of FIG. 2.

Referring to FIG. 19, the interface head of the present invention is preferably used with a single stand-alone thermal agitation unit. As shown in FIG. 11, a single agitation unit may contain 1 cassette 100 and have its own control panel. To be understood however that the interface head may also be used with a fully automated system such as that described in commonly assigned U.S. patent application Ser. No. 09/176,615, filed Oct. 21, 1998, now abandoned, the full disclosure which is incorporated herein for all purposes.

Figure 20:
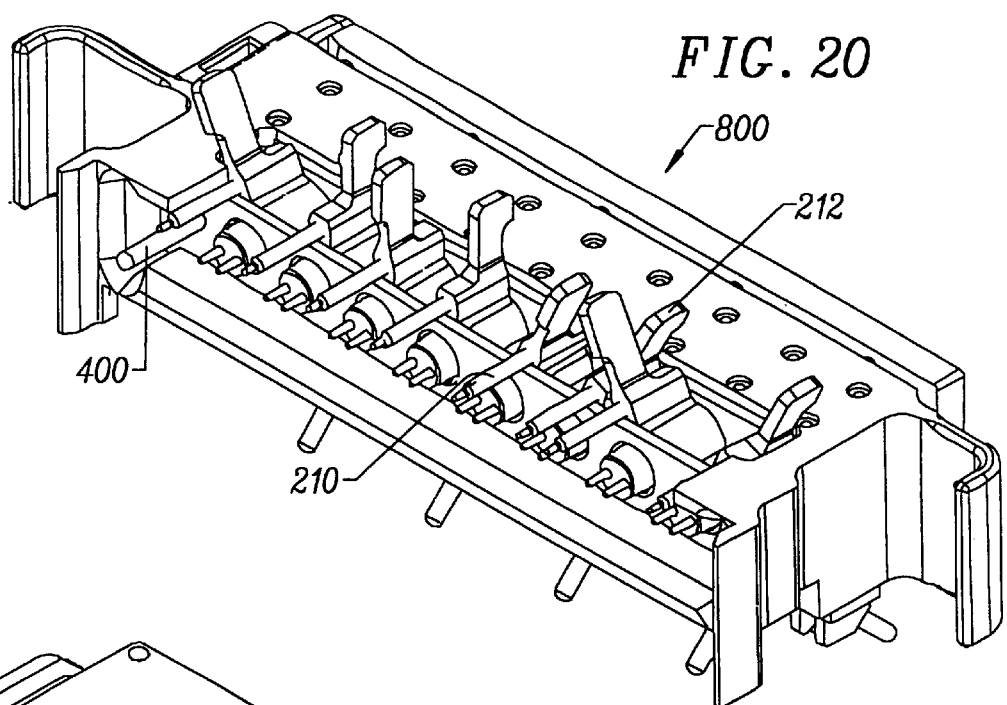
FIGS. 20–21 are perspective views of an interface head for both infusion and extraction.
Figure 21:
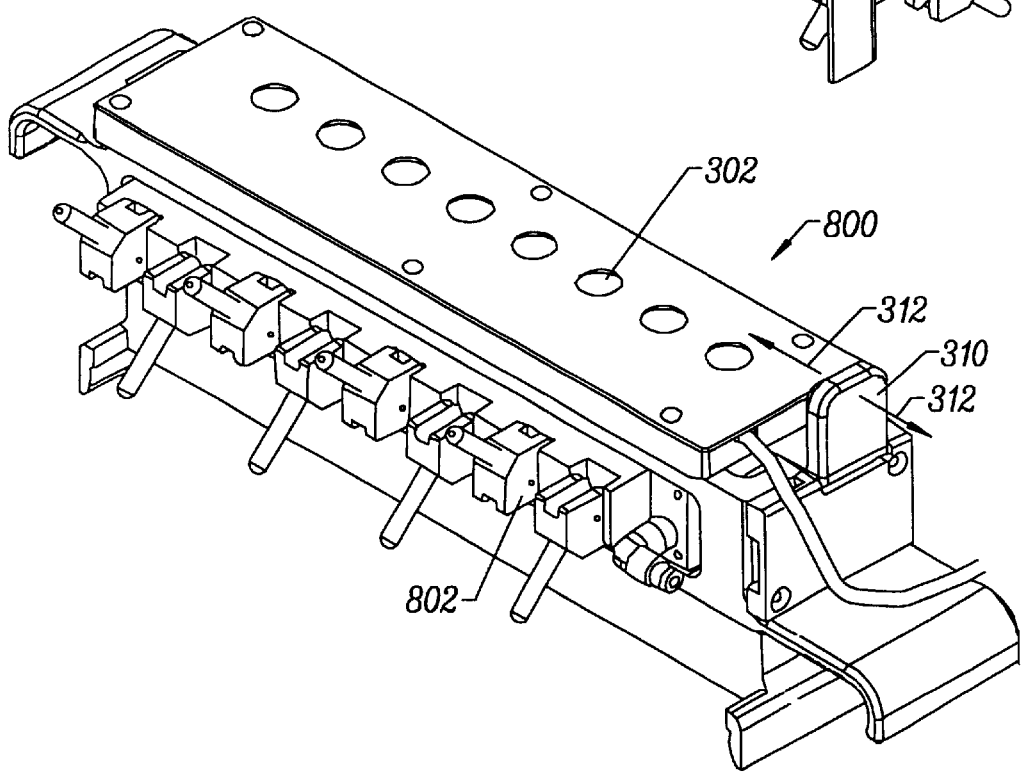

Referring now to FIG. 20, an improved interface head capable of both injection and extraction will be described in further detail. As seen in FIG. 20, the interface head 800 incorporates the pins 210 and handle 212 which are used to open and close the valve cap 110. The interface head 800 also includes the alignment pin 400 which will prevent engagement of the interface head 800 with the cassette lid 120 if the devices are improperly aligned. As seen in FIG. 21, the interface head 800 further includes a plurality of piston valves 802 which can be used to regulate fluid flow from the reaction vessels. The piston valves 802 may be individually actuated to selectively drain fluids from the reaction vessels RV. As seen in FIG. 21, the interface head 800 includes a plurality of syringe/pipette ports 302 which can be opened or closed by sliding the septa valve 310 in the directions as indicated by arrows 312. Materials extracted from the reaction vessels are removed from the interface head through a plurality of tubes 804 which are preferably individually coupled to each extraction port of the interface head. In the preferred embodiment, the interface head 800 allows an operator to manually insert reagents through port 302 into the reaction vessel. The interface head 800 also allows an operator to simultaneously fill the reaction vessels RV with a common solvent or chemical. Fluids inside the reaction vessel RV may also be drained simultaneously or selectively by controlling the positions of the piston valves 802. The interface head 800 simplifies many of these common wash procedures by using a computer controller C which can be programmed to regulate the flow of fluids to and from the reaction vessels through interface head 800.

Figure 22:
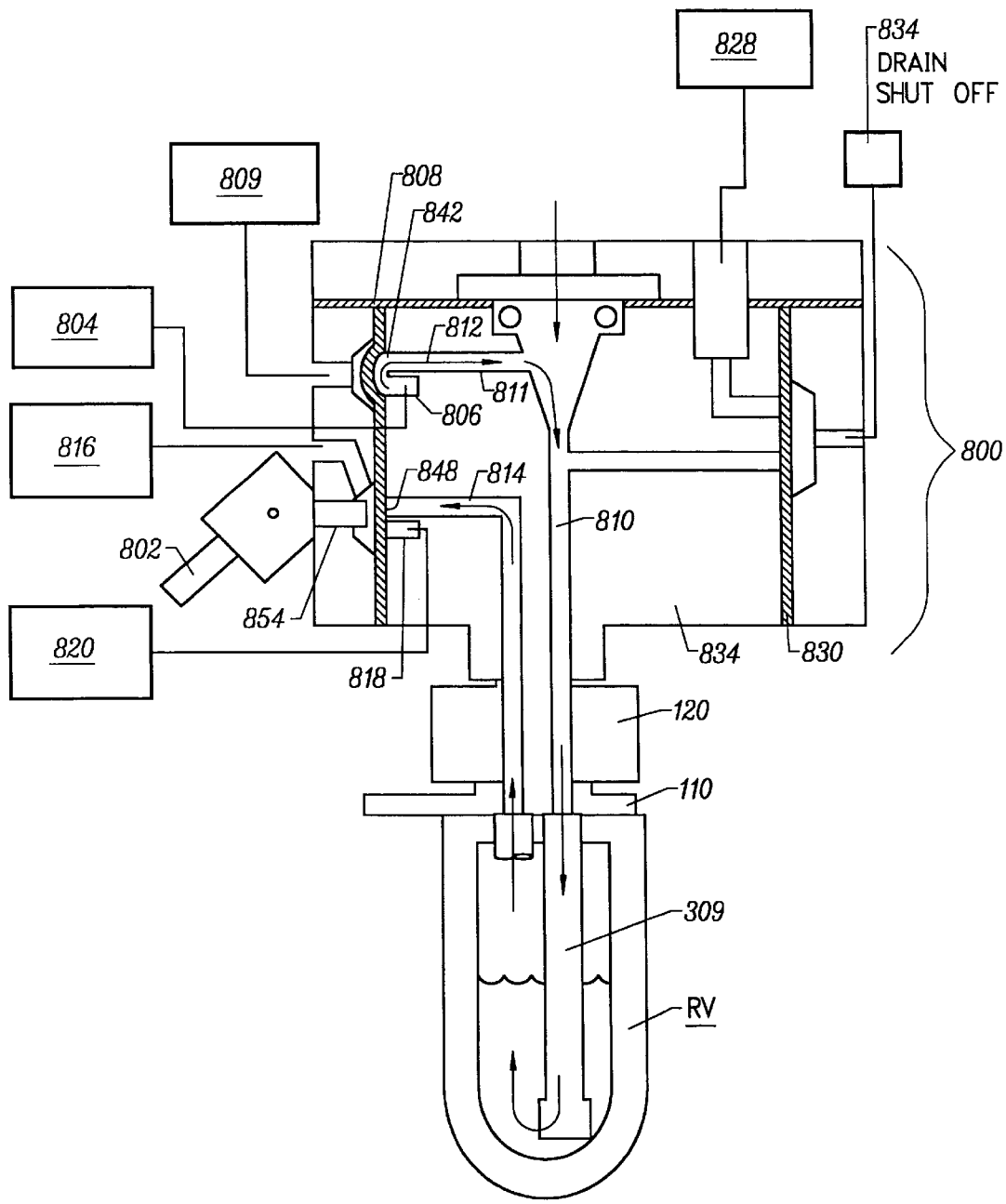
FIGS. 22–23 are cross-section views of the interface head depicting the function of the interface head of FIG. 20.
Figure 23:
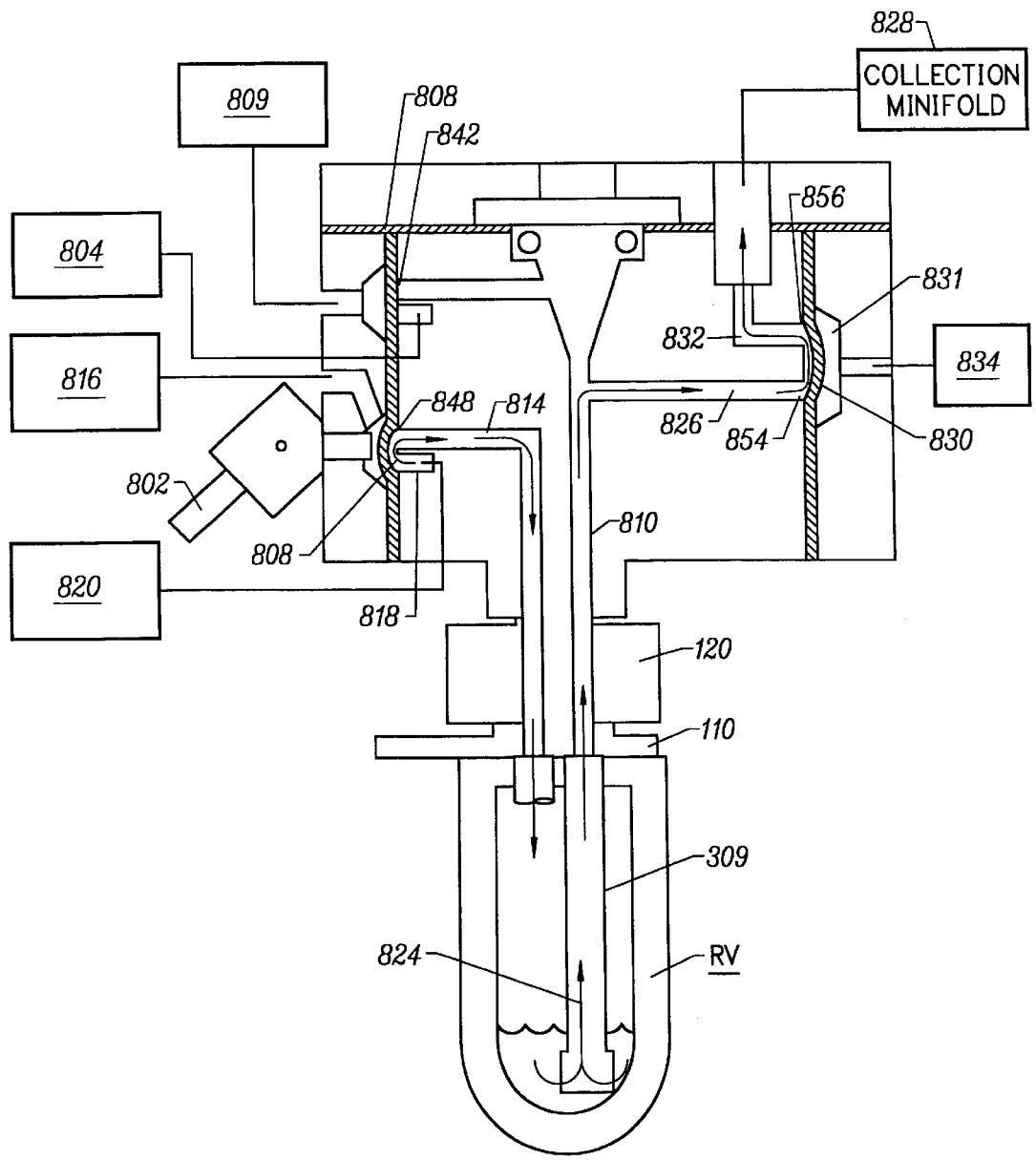

Referring now to FIGS. 22–23, a schematic showing a cross-section of the interface head 800 will be described in further detail. As seen in FIG. 22, the interface head 800 is coupled with a reaction vessel RV. The interface head 800 is coupled to a plurality of pressurized gas and solvent/chemical sources. This allows a computer controller to regulate the common wash cycles used with the interface head 800. FIG. 22 shows the interface head 800 in use to deliver a common wash solvent into the reaction vessel RV. Solvents from the source 804 are directed into the interface head 800 along the common infusion passage 806. Fluid delivered through common passage 806 may be used to simultaneously fill a plurality of reaction vessels RV. Typically, membrane valve 808 prevents fluid in the common infusion passage 806 from entering into the infusion passage 810 and initial inlet passage 811 downstream from the common passage. When gas pressure is released from the pressure/solvent shut-off source 809, the membrane 808 is relaxed as shown in FIG. 22 and fluid may flow from the common passage 806 as indicated by arrow 812 into the infusion passage 810.

In some instances, it is desirable to pulse the shut-off pressure from source 809 against the membrane valve 808 so that a more equal amount of solvent will reach each reaction vessel. Fluid delivered along common passage 806 will tend to flow more easily into those initial inlet passages 811 closest to the fluid source of common passage 806. By repeatedly opening and closing the membrane valve 808 during one filling cycle, fluid will be able to reach the more distal inlet passages 811. For example, when the valve is closed, fluid can fill the entire common passage 806 and pressure may build therein. When the valve 808 is opened, the initial burst of fluid exiting into passages 811 will be roughly equivalent for all of the passages. As flow continues, however, those passages 811 closest to the fluid source of common passage 806 will again start to divert more fluid. The valve 808 is then closed and the process repeated so that fluid can be delivered to the more distant passages 811. When the membrane 808 is not pulsed, more solvent will be introduced into reaction vessels closest to the source 804.

Equal distribution of solvents into the reaction vessels may also be improved by creating back pressure in the reaction vessels which limits the flow of solvent into reaction vessels which have filled more quickly and directing the flow towards those reaction vessels whichever received less solvent and thus created less back pressure. As seen in FIG. 22, the vent passage 814 is also controlled in this embodiment by a portion of membrane 808. During fill cycles, pressurized gas from vent shut-off 816 presses the membrane 808 against the vent passage 814 preventing fluid from flowing from the vent passage to the common vent passage 818. As fluid fills into the reaction vessel RV, the rising amount of solvent in the reaction vessel will increase pressure in the vent passage 814. This back pressure is desirable to allow all the reaction vessels to fill to a substantially even level of solvent. In some scenarios, the membrane 808 covering infusion passage 806 and common vent passage 818 may be pulsed or opened briefly to allow an even amount of back pressure to be released from infusion passages of all the reaction vessels. This is desirable in situations where back pressure in all the reaction vessels have reached a level where solvent flow into the vessel has reached a substantially slowed rate, such as about 0.1 ml/min. Opening and closing the valve 808 releases the back pressure but allows it to build up again to regulate the even distribution of fluids into the reaction vessels. Fluids exiting through the common vent passage is carried to the vent/drain source 820 attached to the interface head 800. During each fill cycle, a membrane valve 808 covering the infusion passage 812 may be pulsed at a substantially higher rate such as between 10 and 20 pulses per fill cycle than the membrane valve 808 covering the vent passage 814 which may be pulsed only once or twice per fill cycle.

As shown in FIG. 3A, diversity reagents or other chemicals may be manually introduced into the interface head 800 through port 302 as indicated by arrow 822. Chemicals introduced through the port 302 will flow into the reaction vessel RV through infusion passage 810. Pressurized gas or solvent may be flowed into the passage 810 after the diversity reagent or chemicals have been introduced. The pressurized gas or solvent will ensure that the diversity reagents which are typically in small quantities, such as about 5 to 1000 $\mu$l, find their way into the reaction vessel. Since each reaction vessel RV may require a different diversity reagent, these chemicals are typically introduced manually into reach reaction vessel. Typically, however, the majority of processing in the reaction vessel comprises solvent washes and the like. Hence, automating the common wash procedure substantially reduces labor on the operator to manually wash each reaction vessel.

Referring now to FIG. 23, when processing is complete, materials in the reaction vessels may be extracted through the interface head 800. As seen in FIG. 23, pressurized gas from the source 820 is supplied to common vent passage 818 and then supplied into vent passage 814. Shut-off pressure from source 816 is removed to allow the membrane 808 to flex, fluidly coupling the passages 818 and 814. The pressurized gas entering the reaction vessel RV will force fluid in the reaction vessel to flow in the direction indicated by arrow 824. The extracted fluid will enter extraction passage 826 which will lead to the collection manifold 828. Membrane valve 830 controls flow between the extraction passage 826 and collection manifold passage 832. By releasing the pressure from the valve shut-off 834, fluid from the reaction vessel RV may flow into the collection manifold 828. The extraction valve 830 may be pulsed in a manner similar to the flat valve 808 covering infusion passage 812 to regulate the flow from the reaction vessel to the collection manifold 828. The piston valve 802 which is typically held in the open position, may be closed to selectively vent some but not all of the reaction vessels coupled to the interface head 800. Placing the valve 802 in the closed position will prevent vent pressure from extracting fluids from the reaction vessel.

Figure 24:
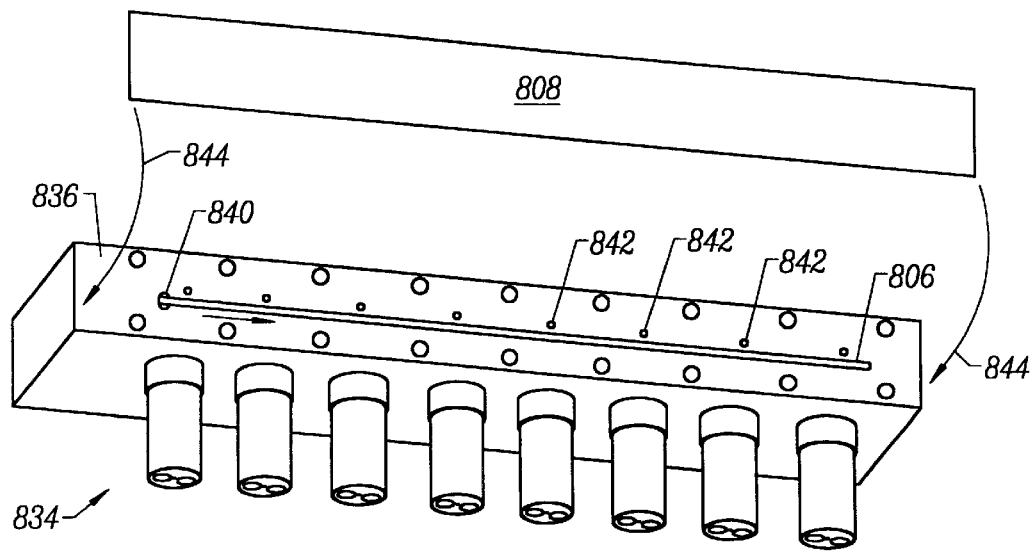
FIGS. 24–25 show a manifold used in an interface head of FIG. 20.
Figure 25:
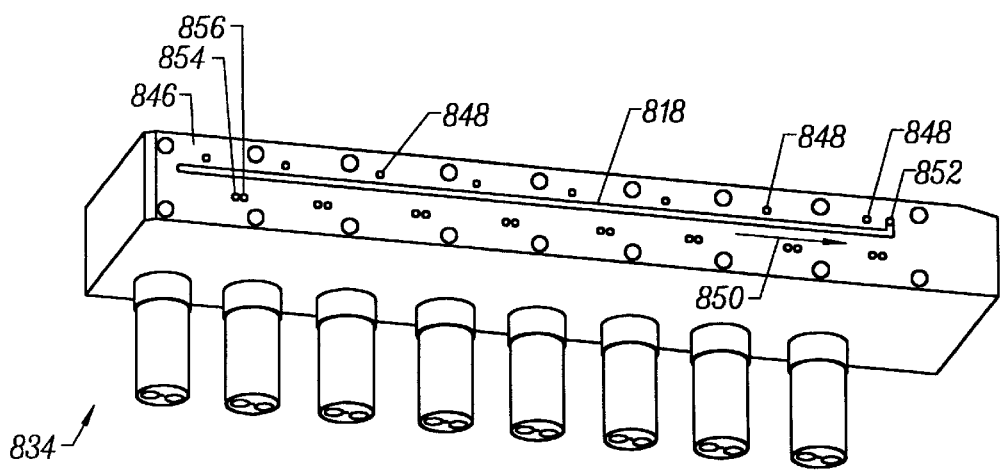

Referring now to FIGS. 24 and 25, the manifold 834 used in the interface head 800 will be described in further detail. FIG. 24 shows the front side of the interface manifold 834. The surface 836 on the manifold 834 has a groove 838 which defines a common infusion passage. The common infusion passage is used to supply wash solvent to each of the reaction vessels coupled to the interface head 800. Fluid introduced through port 840 travels the length of the groove 838 and enters the openings 842 of the inlet passages as can be seen in FIG. 22. When assembled in the interface head 800, the membrane 808 will be positioned as indicated by arrows 844 to substantially cover the surface 836. As described in respect to FIG. 22, the membrane 808 is used to regulate the common introduction of wash solvents into the plurality of reaction vessels. Pressurized gas from source 809 is used to open and close the membrane valve 808.

FIG. 25 shows a backside view of the interface manifold 834. The interface manifold 834 has a backside surface 846. In this embodiment of the manifold 834, a groove in the surface 846 is used to define the common vent passage 818. As seen in FIG. 22, the common vent passage 818 is used to relieve vent pressure from the reaction vessels RV. Vent pressure exiting the vent passages 814 pass from ports 848 into the common vent passage 818. Fluid exiting from the vent passages 814 flow in the direction indicated by arrow 850 to the vent port 852. A membrane similar to membrane 808 as shown in FIG. 24 is positioned over surface 846 to regulate the flow of fluid between the openings 848 and the common vent passage 818. As discussed in regards to FIG. 22, the opening and closing of the membrane valve covering openings 848 and the common vent passage 818 may be regulated by pressurized gas supplied by source 816 or by positioning of the piston 854 of valve 802. The use of pressurized gas from source 816 provides for the simultaneous opening and closing of the vent passages 814 while the piston valve 802 is used to selectively open or close the vent passages individually.

As shown in FIG. 23, fluid flow through the common vent passage 818 may be reversed to introduce pressurized gas into the reaction vessel RV. The pressurized gas is used to extract fluid from the reaction vessels RV in the direction indicated by arrow 824 towards the collection manifold 828. In this scenario, pressurized gas flows from the common vent passage 818 into ports 848 towards reaction vessel RV. Liquid in the reaction vessel RV is forced up the infusion passage 810 as indicated by arrows 824. As liquid enters the extraction passage 826, liquid will encounter membrane valve 830 which controls fluid flow between ports 854 and 856. Pressurized gas from source 834 controls the opening and closing of the membrane valve 830. When pressurized gas is supplied to the chamber 831 fluid flow is stopped between the port 854 and port 856. Typically, pressurized gas from source 834 simultaneously opens or closes all of the ports 854 and 856 on the manifold 834. Fluid flows from port 854 directly into port 856 without entering a common extraction passage which may cause cross-contamination of the materials extracted from each reaction vessel RV.

Although FIGS. 22 and 23 show a cross-section of the interface head 800 depicting all passages in the interface head for ease of illustration, preferred embodiments of the interface head 900 typically has these passages located in different cross-sectional planes to facilitate manufacturing. Referring to FIGS. 26–30, a preferred embodiment of the interface head 900 will be described in further detail. FIG. 26 provides a top-down view of the interface head 900 showing the valves 802 located on the backside of the interface head and handles 212 located on a front side of the interface head to control the position of the cap valves on the reaction vessels RV. Referring now to FIG. 27 which shows a cross-section of the interface head 900 of FIG. 26 along lines 27—27, it can be seen that the infusion passage 810 and extraction passage 826 are located in the same plane of the interface head. FIG. 28 taken along lines 28—28 shows that the vent passage 814 is also located in a different cross-sectional plane. As shown in FIG. 25, the vent passage 814 is positioned to open on to the backside of the interface manifold 834 to facilitate the positioning of the piston valve 802. This differs from the embodiment shown in the schematic of FIG. 22 where the initial inlet passage 811 opens on to the same side as the vent passage 814. FIGS. 29 and 30 show that the initial inlet passage 811 and passage 832 leading to the collection manifold 828 are also located in separate cross-sectional planes of the interface head. As seen in FIG. 29, the initial inlet passage 811 is positioned to carry fluid from the common infusion passage 818 to open at a location just below the septa valve 310. This allows wash solvent introduced from the common infusion passage 818 to wash or carry any diversity reagent just below the septa valve into the infusion passage 810.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, more than one interface head may be used simultaneously with one cassette device. Additionally, the number of tubular members 402 attached to the interface head may also be varied, depending on the desired usage of the head. Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A device for use with a reaction vessel, said device comprising:
    an interface head having a plurality of passageways therein, where said interface head is adapted to removably engage a passage leading into said reaction vessel;
    a septa valve on said interface head comprising an elongate member with a septum portion and a plurality of septum ports, said elongate member slidable between a first position wherein at least one inlet of the passageways in the interface head is sealed by said septum portion and a second position wherein said at least one inlet is aligned with one of said ports to allow delivery of materials from the inlet into the reaction vessel.

2. A device as in claim 1 wherein the interface head further comprises a tubular member coupled to one of said passageways and adapted to engage said passage leading into said reaction vessel.

3. A device as in claim 1 wherein said interface head further comprises a plurality of elastomeric sealing members mounted about said inlet of the passageway in slidable contact with said septa valve.

4. A device as in claim 3 wherein the sealing member comprises an O-ring.

5. A device as in claim 1 wherein said elongate member in said second position aligns said plurality of ports of the septa valve with a plurality of inlets of said passageways in the interface head.

6. A device as in claim 1 wherein said elongate member is slidably mounted within a slot on the interface head, said elongate member having stoppers on a distal end and proximal end of the member to limit the range of motion of the member.

7. A device as in claim 1 wherein the septum comprises a layer of sealing material coupled with a layer of chemically inert and protective material.

8. A device as in claim 1 wherein the septum comprises a layer of silicone coupled to a layer of Teflon®.

9. A device as in claim 1 wherein the septa valve is slidably mounted on said interface head to simultaneously cover a plurality of said inlets.

10. An interface head for use with a reaction vessel, said interface head comprising:
    at least one passageway therein, the passageway having an upper end; and
    a septa valve, the septa valve comprising a member having a septum portion and at least one septum port, said member slidable between
        a first position wherein said upper end of the passageway is sealed by said septum portion and
        a second position wherein said upper end of the passageway is unsealed by said septum port,
    said interface head adapted to removably engage a passage leading into said reaction vessel.

11. The interface head of claim 10, further configured to allow the transfer of materials between the passageway and the reaction vessel.

12. The interface head of claim 10, wherein the passageway is configured to deliver material toward the reaction vessel.

13. The interface head of claim 10, wherein the passageway is configured to deliver material away from the reaction vessel.

14. The interface head of claim 10 further comprising a pin that mates with a cap of the reaction vessel.

15. The interface head of claim 10, further comprising a port that delivers material to the passageway.

16. The interface head of claim 10, further comprising a port that vents material away from the passageway.

17. The interface head of claim 10, further comprising at least one guide pin to facilitate alignment of the interface head with a housing containing the reaction vessel.

18. The interface head of claim 10, wherein the septum portion is penetrable by a piercing device.

19. The interface head of claim 10, wherein the passageway is configured to receive an instrument for delivering material into, or extracting material from, the passageway when the septa valve is in the second position.

20. The interface head of claim 10, wherein the interface head comprises aluminum.

21. The interface head of claim 10, wherein the interface head comprises polyphenyl sulfide.

22. The interface head of claim 10, further configured to be manually operated.

23. The interface head of claim 10, further configured to be mounted on a robotic manipulator for automated operation.

* * * * *